United States Patent
Drobnik et al.

(10) Patent No.: US 8,641,593 B2
(45) Date of Patent: Feb. 4, 2014

(54) BRACHYTHERAPY ELEMENT TRANSFER SYSTEM

(75) Inventors: Christopher Drobnik, Waconda, IL (US); Michael Drobnik, Downers Grove, IL (US); Breese Watson, Highland Heights, OH (US)

(73) Assignee: C. R. Bard, Inc., Murray Hill, NJ (US)

( * ) Notice: Subject to any disclaimer, the term of this patent is extended or adjusted under 35 U.S.C. 154(b) by 699 days.

(21) Appl. No.: 12/529,153

(22) PCT Filed: Feb. 28, 2008

(86) PCT No.: PCT/US2008/055253
§ 371 (c)(1),
(2), (4) Date: Jun. 25, 2010

(87) PCT Pub. No.: WO2008/106586
PCT Pub. Date: Sep. 4, 2008

(65) Prior Publication Data
US 2010/0268015 A1    Oct. 21, 2010

Related U.S. Application Data

(60) Provisional application No. 60/892,079, filed on Feb. 28, 2007.

(51) Int. Cl.
*A61M 36/00* (2006.01)
(52) U.S. Cl.
USPC .................................................. 600/7; 600/4
(58) Field of Classification Search
USPC ........... 600/1–8, 426, 439; 604/57, 62, 93.01, 604/116, 506; 24/11 R
See application file for complete search history.

(56) References Cited

U.S. PATENT DOCUMENTS

| 5,683,345 | A  |   | 11/1997 | Waksman et al. |
|-----------|----|---|---------|----------------|
| 6,007,474 | A  | * | 12/1999 | Rydell .............................. 600/7 |
| 6,010,466 | A  |   | 1/2000  | McGeorge |
| 6,061,588 | A  |   | 5/2000  | Thornton et al. |
| 6,221,003 | B1 |   | 4/2001  | Sierocuk et al. |
| 6,450,937 | B1 | * | 9/2002  | Mercereau et al. .............. 600/7 |
| 6,458,070 | B1 |   | 10/2002 | Waksman et al. |
| 6,503,185 | B1 |   | 1/2003  | Waksman et al. |
| 6,821,242 | B1 |   | 11/2004 | Waksman et al. |
| 6,969,344 | B2 |   | 11/2005 | Drobnik et al. |
| 7,160,238 | B1 |   | 1/2007  | Waksman et al. |

(Continued)

FOREIGN PATENT DOCUMENTS

AU    710209 B2    9/1999
BR    9509138 A    11/1998

(Continued)

OTHER PUBLICATIONS

Aug. 15, 2008 International Search Report in internatioal application No. PCT/US2008/55253.

(Continued)

*Primary Examiner* — Charles A Marmor, II
*Assistant Examiner* — Laura Fajardo
(74) *Attorney, Agent, or Firm* — Rutan & Tucker, LLP

(57) ABSTRACT

Disclosed herein is a system for transferring brachytherapy elements to a needle, such as seeds, connectors, spacers, and strands. The system comprises a transfer device and, optionally, a stylet and a rack configured to hold one or more transfer devices.

18 Claims, 3 Drawing Sheets

(56) References Cited

U.S. PATENT DOCUMENTS

| | | | |
|---|---|---|---|
| 2003/0018233 A1* | 1/2003 | Miller | 600/7 |
| 2003/0229259 A1 | 12/2003 | Waksman et al. | |
| 2004/0192999 A1 | 9/2004 | Waksman et al. | |
| 2007/0002174 A1 | 1/2007 | Wei et al. | |
| 2007/0021714 A1 | 1/2007 | Miller | |
| 2007/0265488 A1* | 11/2007 | Lamoureux et al. | 600/7 |

FOREIGN PATENT DOCUMENTS

| | | |
|---|---|---|
| CA | 2203362 A1 | 5/1996 |
| CA | 2362530 A1 | 5/1996 |
| CA | 2362559 A1 | 5/1996 |
| CA | 2362617 A1 | 5/1996 |
| CN | 1167446 A | 12/1997 |
| DE | 69534167 T2 | 3/2006 |
| EP | 0790844 A1 | 8/1997 |
| EP | 1221324 A1 | 7/2002 |
| EP | 2125098 B1 | 9/2012 |
| JP | 2003135606 A | 5/2003 |
| WO | 9613303 A1 | 5/1996 |
| WO | 2007047280 A2 | 4/2007 |

OTHER PUBLICATIONS

Sep. 1, 2009 International Preliminary Report on Patentability in international application No. PCT/US2008/55253.

Aug. 6, 2008 Written Opinion of the International Searching Authority in international application No. PCT/US2008/55253.

EP 08 754 831.9 filed Jul. 28, 2009 Examination Report dated Feb. 16, 2011.

EP 08 754 831.9 filed Jul. 28, 2009 Extended European Search Report dated May 5, 2010.

EP 08 754 831.9 filed Jul. 28, 2009 Intent to Grant dated May 4, 2012.

* cited by examiner

BRACHYTHERAPY ELEMENT TRANSFER SYSTEM

This application is a U.S. national stage application under 35 U.S.C. §371 of International Application No. PCT/US2008/055253, filed Feb. 28, 2008, claiming priority to U.S. Provisional Application No. 60/892,079, entitled "Brachytherapy Element Transfer System," filed Feb. 28, 2007, each of which is incorporated herein by reference in its entirety into this application.

Victims of cancer are often treated using chemotherapy and/or radiation therapy. Chemotherapy is the treatment of cancer using drugs that destroy cancer cells. Radiation therapy is the use of a type of energy, called ionizing radiation, to destroy cancer cells.

Brachytherapy is one type of radiation therapy used to treat cancer. Brachytherapy involves placing a small amount of radioactive material inside the body, near the cancer cells or tumor. Unlike external radiation treatment such as electron beam irradiation, brachytherapy enables a doctor to use a higher total dose of radiation to treat a small area in a shorter amount of time. Brachytherapy may be temporary or permanent. In temporary brachytherapy, radioactive material is placed near the cancer cells or tumor for a fixed period of time, and then withdrawn. In permanent brachytherapy, radioactive material in the form of "seeds" is permanently placed near the cancer cells or tumor. Although the seeds remain in the body permanently, the radiation levels of the seeds drop off over time Brachytherapy has been used in the treatment of numerous types of cancer, including cervical, breast, lung, head and neck, and prostate. For example, prostate cancer may be treated using radioactive seeds, such as $Pd^{103}$ or $I^{125}$ seeds Depending on the prostate size and aggressiveness of the cancer, a health care provider can determine the number and positioning of the radioactive seeds needed to deliver a sufficient amount of radiation to kill the cancerous cells. In certain brachytherapy delivery systems, the requisite number of radioactive seeds, separated by bio-absorbable spacers and/or bio-absorbable connectors, are loaded into brachytherapy needles and inserted into the prostate. Once the tip of the needle has been placed in its proper position, the needle is withdrawn, leaving a pattern of seeds, spacers and/or connectors.

Proper seed placement and seed retention at the implantation site influence the success or failure of a brachytherapy procedure. Certain seed implantation devices and methods often provide variable seed spacing and dosimetric patterns during and after implantation Loose seeds, especially those that are extra-capsular (located outside the capsule of the prostate), tend to migrate within the patient, and as a result, may not provide radiation where needed and may sometimes cause damage to other radiation-sensitive areas of the body. In addition, the manual loading of seeds and spacers into the brachytherapy needle can be a laborious and time-consuming task.

As a result of the above, "stranded" seeds have been developed. Stranded seeds are connected together by connective material to form a strand. The seeds in a particular strand may be spaced apart by a predetermined interval to create a desired dosing level. By varying the spacing of seeds and the lengths of strands, strands can be formed with different desired dosing levels. It may be advantageous to provide pre-constructed strands packaged in accordance with a patient's particular dose plan. Such packaging is disclosed in PCT Application Publication No. WO 2007/047280, the disclosure of which is incorporated herein by reference in its entirety as if fully set forth herein.

To facilitate the formation of strands of seeds, a brachytherapy seed deployment system has been disclosed in U.S. Pat. Nos. 6,010,446; and 6,969,344 (the contents of each of which are incorporated by reference as if fully set forth herein). The system comprises a basic unit of at least two seeds and a connecting spacer joining the seeds to maintain proper spacing between the seeds. Further alternating connecting spacers and seeds may be connected to this basic unit to form a strand of seeds, each seed separated from adjacent seeds by the length of the connecting spacer. The length of the connecting spacers and the overall length of the strand may be varied to create a desired dosing level depending on patient needs. The connectors may be formed of solid rods of bioabsorbable material that degrade within 18-24 months after being inserted into the body.

FIG. 1 illustrates three components of an exemplary brachytherapy seed deployment system designed to provide seed spacing in 0.5 cm increments. Reference character 100 designates an exemplary 1 cm standard connector (which is the distance between the center of the seeds when they are seated in cups 101A and 101B), reference character 110 designates an exemplary 0.5 cm seed-to-seed connector having cups 111A and 111B, and reference character 120 designates an exemplary extension connector having 0.5 cm center-to-center seed spacing beyond 1 cm, with the extension feature 112 being configured to seat within cups 101A-B, 111A-B, and 121. Used together, these components may form strands of certain lengths with certain seed spacings. Certain devices can be used to assemble the strands in the operating room, such as the SourceLink™ manual loader and the QuickLink® delivery system.

To apply these strands to the cancer cells or tumor, a hollow tube delivery device such as a needle, catheter or applicator may first be inserted into the affected area. Strands are then placed in the delivery device the delivery device is drawn out and the strands are seated in the proper location. Alternatively, the strands may first be placed into the delivery device prior to the insertion of the delivery device into the body. X-rays, ultrasound or CT scans may be among the tools used to ensure that the seeds in the strands are properly placed.

The transfer of the radioactive elements (including stranded and loose seeds) to the hollow tube delivery device can be problematic. During the transfer, the healthcare provider may be unnecessarily exposed to radiation from the radioactive elements Furthermore, strands can be damaged or dropped during transfer to the hollow tube delivery device. It could be desirable to provide a transfer device that at least partially shields the healthcare provider from radiation.

SUMMARY

According to one embodiment of the present disclosure, there is provided a brachytherapy element transfer device comprising a hollow cannula defining a lumen, wherein said cannula has a proximal end and a distal end, said distal end being configured to communicate with the proximal end of a brachytherapy device; and at least one gating feature disposed within said lumen, wherein said gating feature is configured to at least partially occlude said lumen. The term "communicate" means that the lumen of the transfer device at least substantially aligns with the lumen of the hollow cannula.

According to another embodiment of the present disclosure, there is provided a brachytherapy element transfer system comprising a plurality of brachytherapy element transfer devices comprising a hollow cannula defining a lumen, wherein said cannula has a proximal end and a distal end, said distal end being configured to communicate with the proximal end of a brachytherapy device; at least one stylet; and at least one device configured to hold the plurality of brachytherapy transfer devices in a configuration that is associated with a treatment plan for a patient.

According to another embodiment of the present disclosure, there is provided a method for implanting at least one brachytherapy element in a patient, comprising determining the brachytherapy needle loading configuration per the patient dose plan; inserting the at least one brachytherapy element into a brachytherapy element transfer device comprising a hollow cannula defining a lumen, wherein said cannula has a proximal end and a distal end, said distal end being configured to communicate with the proximal end of a brachytherapy device; placing the loaded brachytherapy element transfer device into a rack; repeating the foregoing steps until the rack contains at least substantially the entire patient dose plan; inserting a plurality of brachytherapy needles into the region in which the at least one brachytherapy element is to be implanted; placing the distal end of a loaded brachytherapy element transfer device against the proximal end of the brachytherapy needle; and, using a stylet, urging the at least one brachytherapy element from the brachytherapy element transfer device into the brachytherapy needle

BRIEF DESCRIPTION OF THE DRAWINGS

The drawings are illustrative of certain embodiments of the present invention, in which like characters represent like elements throughout the views of the drawings, and wherein:

FIG. 6 illustrates another embodiment of an implant needle transfer device in accordance with the present disclosure.

DESCRIPTION

The transfer device is used to transfer elements, such as radioactive and non-radioactive elements, including but not limited to radioactive seeds, such as BrachySource® $I^{125}$ seeds and IheraSeed® $Pd^{103}$ seeds. It should be noted that seeds comprising other radioactive material can be used as well, including but not limited to $Cs^{131}$, $Au^{198}$, $Co^{60}$, $Ir^{192}$, and combinations of any of the foregoing. Non-limiting examples of other elements include non-radioactive connectors, non-radioactive spacers, and assembled strands, such as assembled SourceLink® strands, configured for insertion into a medical device, for example a brachytherapy implant needle. According to various embodiments, the transfer device will provide shielding and product protection during the transfer process. According to various embodiments, the transfer device can be used with loaders such as the QuickLoad™ and SourceLink™ manual loaders, the QuickLink® delivery system, with the ReadyLink® Delivery System (all of C R. Bard, Inc., Covington, Ga.), and with manually assembled components.

The transfer device can be configured to transfer strands or loose components into various types of devices, for example needles, such as hubbed needles (so named for the hub at the proximal end) and applicator needles (designed for use with the Mick® Applicator (Mick Radio-Nuclear Instruments, Inc., Mt. Vernon, N.Y.)). By way of non-limiting example, needles suitable for use with the transfer device include the Bard® BrachyStar® FastFill® Needle and the Bard® BrachyStar® Applicator Seed Implant Needle, respectively (C.R. Bard, Inc., Covington, Ga.). According to various embodiments, the transfer devices disclosed herein can be used with other types of needles and containers as well.

According to various embodiments, the transfer devices in accordance with the present disclosure can be provided in a number of different embodiments For example, disclosed herein are transfer devices configured for use with both implant needles and applicator needles. According to various embodiments, the transfer devices disclosed herein may have at least one gating feature. The gating feature functions to retain the brachytherapy element within the transfer device during transfer of the element to the needle The present invention will now be described by reference to more detailed embodiments, with reference to the accompanying drawings. This invention may, however, be embodied in different forms and should not be construed as limited to the embodiments set forth herein. Rather, these embodiments are provided so that this disclosure will be thorough and complete, and will fully convey the scope of the invention to those skilled in the art.

Figure 1:
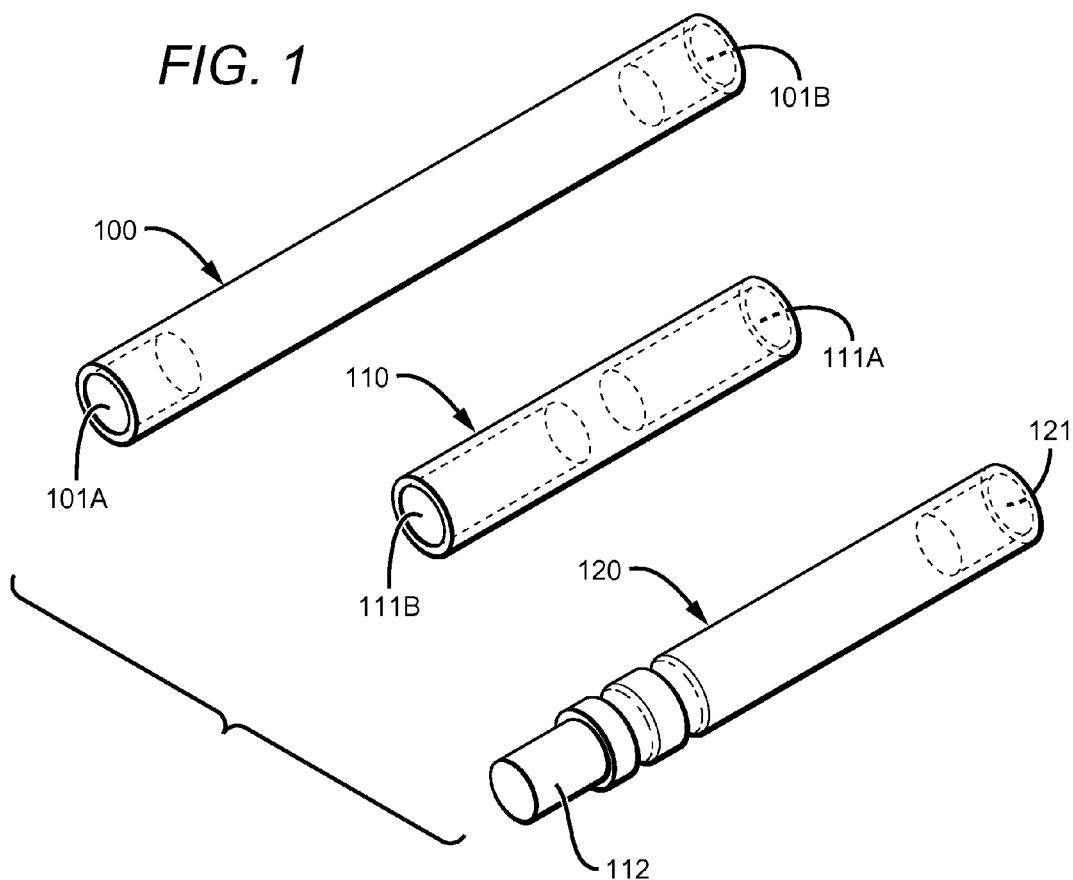
FIG. 1 illustrates connecting spacers.
Figure 2:
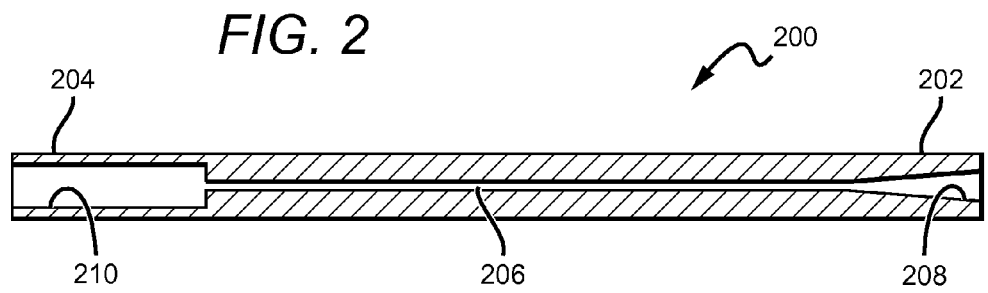
FIG. 2 illustrates one embodiment of an applicator needle transfer device in accordance with the present disclosure.

One embodiment of an applicator needle transfer device 200 is illustrated in FIG. 2, defined by a generally tubular member with proximal end 202 and distal end 204 that communicate with each other via a lumen 206 extending the entire length of the device. Lumen 206 has a funnel-shaped proximal end 208. This funnel-shaped feature serves to axially align brachytherapy elements, such as a strand. In addition, the funnel-shaped feature 208 can be configured to mate with the QuickLink™ or SourceLink® loaders. That is, once seeds and connectors are joined to form a strand by the loader, the proximal end 202 of the transfer device can receive the strand directly from the loader. The distal end 210 of lumen 206 is designed to fit the proximal end of an applicator needle hub, so that the axially aligned elements (in the form of, e.g., a strand) can be urged into the needle.

Figure 3:
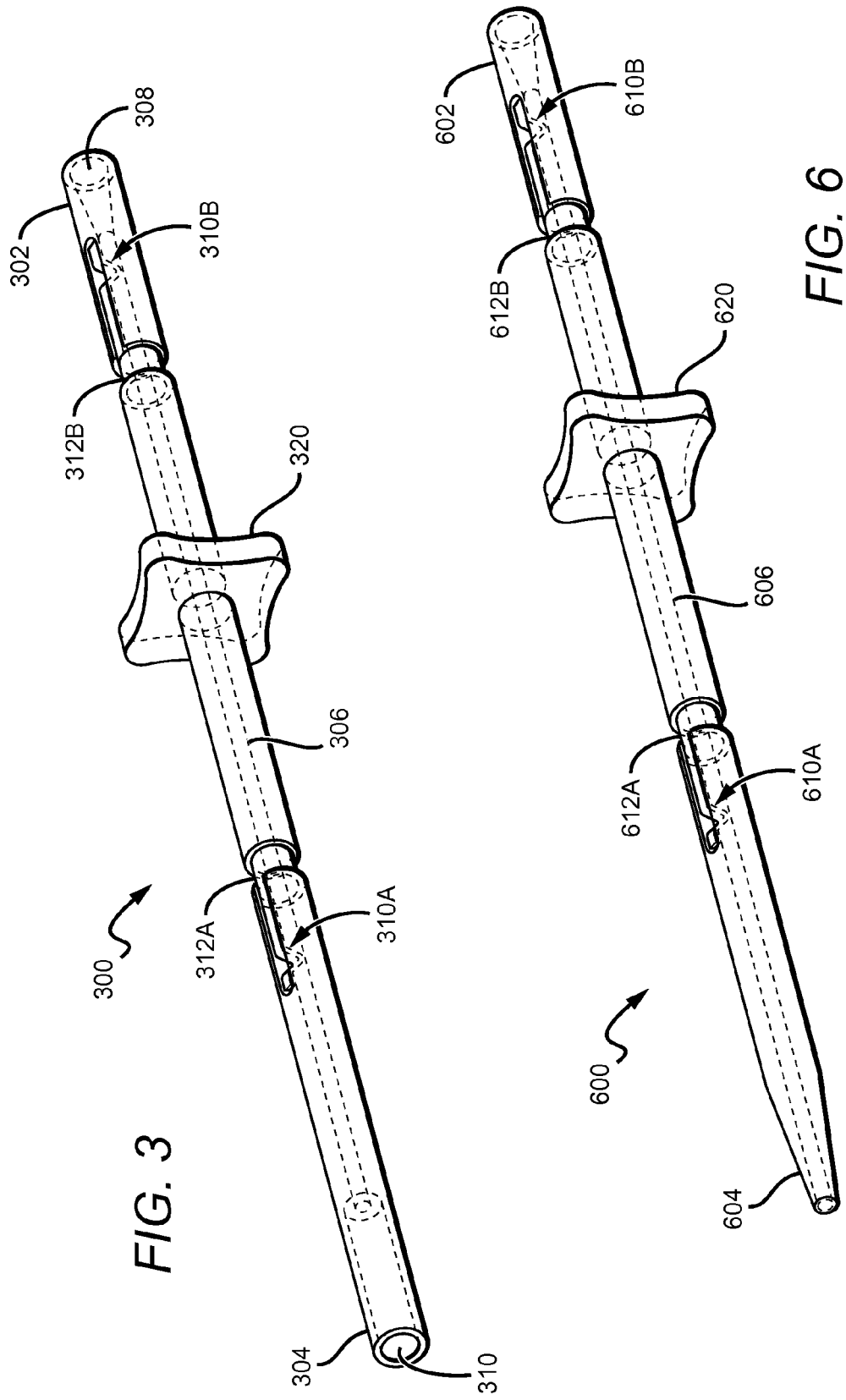
FIG. 3 illustrates another embodiment of an applicator needle transfer device in accordance with the present disclosure.
Figure 4:
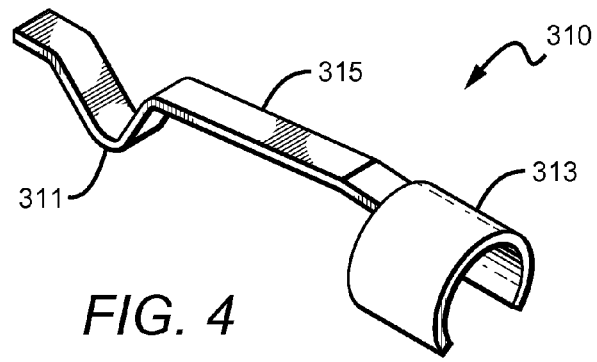
FIG. 4 illustrates one embodiment of a gating feature in accordance with the present disclosure.

According to various embodiments, the device 200 can also comprise a stainless steel grip 320 (illustrated in FIG. 3). The grip can be seamlessly brazed to the tubular member FIG. 3 illustrates another embodiment of an applicator needle transfer device in accordance with the present disclosure. The transfer device 300 has a proximal end 302, a distal end 304, a lumen 306, and two gating features 310A and 310B. Gating features 310A-B are biased inwardly, so that they at least partially occlude lumen 306. The gating feature is further illustrated in FIG. 4. It includes an occlusive feature 311, an arm 315, and a feature 313 that snaps into indentations 312A-B (FIG. 3). The arm 315 is angled relative to the longitudinal axis of gating feature 310 so that occlusive feature 311 is biased into lumen 306 (FIG. 3).

In operation, and by way of non-limiting example, a strand (not shown) is placed in funnel-shaped portion 308 of lumen 306. The strand is gently urged into the gating feature 310B via a stylet (not shown). Upon application of a certain amount of force, the gating feature is forced upward by the distal end of the strand, so that the gating feature no longer occludes lumen 206. Once the entire strand is urged past gating feature 310B, the stylet is withdrawn and the strand is locked between gating features 310A and 310B The loaded transfer device can then be manipulated without concern that the strand will unintentionally depart the device. When the strand is ready to be urged into a needle, distal end 304 of the transfer device is placed over the proximal end of the needle (not shown). The stylet is introduced into proximal end 302, forcing open gate 310B, and urging the strand past gate 310A.

Figure 5:
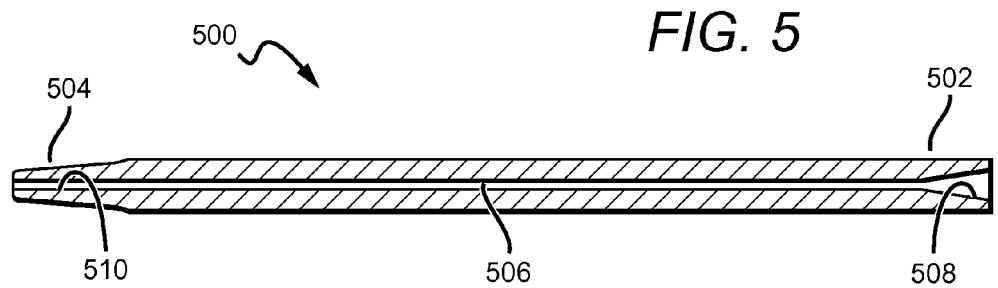
FIG. 5 illustrates one embodiment of an implant needle transfer device in accordance with the present disclosure.

FIG. 5 illustrates a transfer device 500 for an implant needle. Transfer device 500 includes a proximal end 502 and a distal end 504. Lumen 506 has a funnel-shaped proximal portion 508. The distal end 504 has a conical shape configured for placement in the hub at the proximal end of an implant needle (not shown).

FIG. 6 illustrates an embodiment of an implant needle transfer device 600, comprising a proximal end 602, a distal end 604, a gripping feature 620, gating features 610A and 610B, and features 612A and 612B configured for mounting the gating features. As with the applicator needle, although two gating features are shown, transfer devices having no gating features, or only a single gating feature, are also contemplated by the present disclosure.

Figure 7:
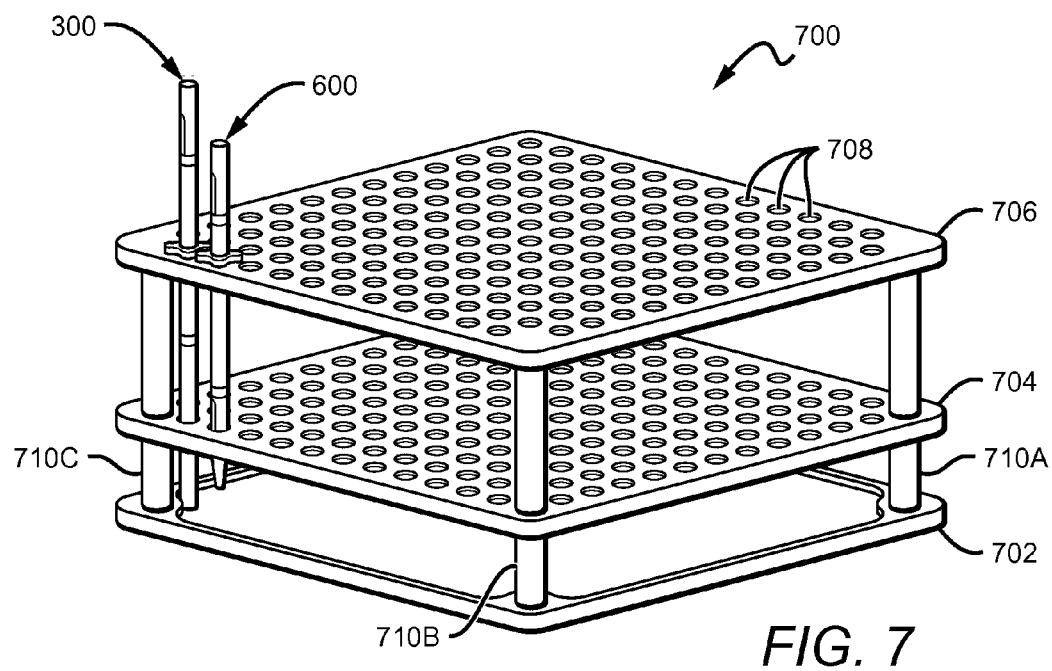
FIG. 7 illustrates one embodiment of a rack configured to hold at least one transfer device in accordance with the present disclosure.

According to various embodiments, the needles can be loaded either before implantation or after they have been placed into the patient (i.e., as part of an after-loading technique). In addition to transfer devices, the system for transferring radioactive elements can also comprise a rack configured to hold a given number of transfer devices during storage, steam sterilization and/or the implant procedure. The rack can have a hole pattern to mimic the hole pattern on standard needle templates used in the implant procedure, so that loaded transfer devices can be staged in such a way that there is a visual cue to the needles to be loaded. The rack can have blank areas where the hole positions can be marked (e.g. to number the holes A1, A2, etc.) to match the naming of the grid positions in a particular dose planning software system. An exemplary embodiment of such a rack is illustrated in FIG. 7. Rack 700 comprises a base plate 702, a first guiding plate 706, a second guiding plate 704, and supporting columns 710A, 710B, and 710C (and a fourth column, not shown) As illustrated, the rack 700 contains transfer devices 300 and 600 disposed in holes 708.

According to various embodiments, a stylet is used with the transfer devices disclosed herein According to various embodiments, when the transfer device is mated to a needle in the after-loader technique, a stylet is provided which is configured to allow the strand to be implanted immediately, rather than pushing the strand out of the transfer device into the needle, removing the transfer device, and replacing the original needle stylet back into the implant needle. According to another embodiment, however, once the needle is loaded with the brachytherapy element, the transfer device can be withdrawn from the proximal end of the needle, and the needle stylet can be re-inserted to facilitate implantation of the brachytherapy element in the patient According to various embodiments, the transfer device stylet is at least as long as the combined length of the transfer device and the needle.

The transfer devices disclosed herein can be made from a variety of materials. According to various embodiments, the transfer devices are machined from stainless steel. The transfer devices can have any size suitable for their intended purpose According to various embodiments, an exemplary transfer device can have a length ranging from 5 to 25 cm, for example 7 to 20 cm, including 10 to 15 cm, for example 13 to 15 cm, such as 14 cm. The transfer devices can have an outside diameter ranging from 0.1 to 1 cm, such as 0.3 to 0.7 cm, for example 0.5 cm. The internal lumen can have any diameter configured for receiving brachytherapy elements, including radioactive seeds and non-radioactive connectors/spacers. According to various embodiments, the internal diameter ranges from 1 to 3 mm.

The transfer devices disclosed herein are not limited in the way in which they can be used in medical procedures. For example, and with reference to a brachytherapy procedure, the healthcare provider would want to select the correct transfer device for the implant needle type used during the procedure (i.e., implant or applicator needle). A needle loading configuration is determined with reference to the patient's dose plan, and the configuration is prepared per typical protocol. The prepared seed load configuration is then transferred into the transfer device, either manually or via a loading system outlet adaptor.

Next, the transfer device can be placed in a rack, such as rack 700 (FIG. 7). According to various embodiments, the hole positions on the rack may be labeled to correspond to the numbering system used in the needle template and/or dose planning software.

According to various embodiments, the foregoing steps can be repeated until all the needle loads have been prepared and transferred into the transfer devices and placed in the rack. Next, under ultrasonic guidance, a plurality of needles are located in the desired treatment area (e.g., the prostate gland, or any other tissue to be treated). The transfer device corresponding to a particular needle is removed from the rack to implant the desired needle. The distal end of the transfer device is inserted into or onto the proximal end of the needle. A stylet is employed to push the needle load through the transfer device and into the needle. Once it has been verified that the needle load is at the needle tip, the stylet is held in position while pulling back on the needle/transfer device assembly to place the needle load where desired. The stylet/transfer device/needle assembly is then removed.

According to various embodiments, the transfer devices can be loaded by a pharmacy according to a particular patient's dose plan. The loaded devices can then be shipped to the facility that will implant the brachytherapy elements into the patient.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how several forms of the invention may be embodied in practice.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are expressly incorporated by reference in their entirety Also, unless otherwise indicated, all numbers expressing quantities of physical parameters and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Numerical ranges given throughout this specification will include every narrower numerical range that falls within such broader numerical range, as if such narrower numerical ranges were all expressly written herein.

What is claimed is:

1. A method of preparing a brachytherapy treatment, comprising:
   a. determining a brachytherapy device loading configuration per a patient dose plan;
   b. inserting one or more than one brachytherapy elements into a brachytherapy element transfer device according to the brachytherapy device loading configuration to form a loaded brachytherapy element transfer device, the loaded brachytherapy element transfer device comprising a cannula defining a lumen and a gating feature at least partially occluding the lumen in an occlusive position, wherein the gating feature includes an attachment feature, an arm, and an occlusive feature, and wherein the attachment feature attaches to an outer surface of the cannula by snapping the attachment feature into an indentation on the outer surface of the cannula, and the arm is angled relative to the longitudinal axis of the gating feature so that the occlusive feature is biased into the lumen, and wherein the loaded brachytherapy element transfer device is configured for use by placing a distal end of the cannula against a proximal end of a brachytherapy needle that is inserted into a region in which the brachytherapy elements are to be implanted, the cannula and the brachytherapy needle in communication such that use of a stylet can urge the at least one brachytherapy element against the gating feature such that the gating feature moves into a non-occlusive position, past the gating feature, and from the loaded brachytherapy element transfer device into the brachytherapy needle;
   c. placing the loaded brachytherapy element transfer device into a rack in a configuration corresponding to the patient dose plan; and
   d. repeating steps b-c for at least one additional brachytherapy element transfer device until the rack contains at least substantially the patient dose plan.

2. The method according to claim 1, wherein inserting one or more than one brachytherapy elements into the brachytherapy element transfer device is done by inserting the one or more than one brachytherapy elements into the brachytherapy element transfer device through a proximal end opening of the cannula.

3. The method according to claim 1, wherein a proximal end of the cannula is configured to mate with a brachytherapy element loader, and inserting one or more than one brachytherapy elements into the brachytherapy element transfer device is done by inserting the one or more than one brachytherapy elements into the brachytherapy element transfer device through a proximal end of the cannula using a brachytherapy element loader mated to the proximal end of the cannula.

4. The method according to claim 1, wherein the rack includes a hole pattern that mimics a needle template hole pattern, and wherein placing the loaded brachytherapy element transfer device into a rack in a configuration corresponding to the patient dose plan includes staging the loaded brachytherapy element transfer device in the rack in such a way that there is a visual cue as to which brachytherapy needle should be used with the loaded brachytherapy element transfer device.

5. The method according to claim 1, wherein the rack includes blank areas configured for marking hole positions to match the naming of grid positions of the patient dose plan, and wherein placing the loaded brachytherapy element transfer device into a rack in a configuration corresponding to the patient dose plan includes marking at least one hole position in at least one of the blank areas to match the naming of a grid position of the patient dose plan and staging the loaded brachytherapy element transfer device in the rack in such a way that the marked blank area provides a visual cue as to which brachytherapy needle should be used with the loaded brachytherapy element transfer device.

6. The method according to claim 1, further comprising sterilizing multiple loaded brachytherapy element transfer devices while the multiple loaded brachytherapy element transfer devices are held in the rack.

7. The method according to claim 1, wherein only the one or more than one brachytherapy elements and the gating feature are within or partially within the lumen when the loaded brachytherapy element transfer device is not connected to a brachytherapy needle or a brachytherapy element loader.

8. The method according to claim 1, wherein the gating feature is positioned proximate to the distal end of the cannula and a separate second gating feature is positioned proximate to a proximal end of the cannula, and wherein inserting the one or more than one brachytherapy elements into the brachytherapy element transfer device includes urging the one or more than one brachytherapy elements into the second gating feature such that the second gating feature is forced radially outward by the one or more than one brachytherapy elements and urging the one or more than one brachytherapy elements past the second gating feature until the one or more than one brachytherapy elements are locked between the first gating feature and the second gating feature.

9. A method of treating a patient using brachytherapy, comprising:
   a. determining a patient dose and treatment plan;
   b. obtaining a rack having a plurality of brachytherapy element transfer devices held in a configuration corresponding to the patient dose and treatment plan, each of the plurality of brachytherapy element transfer devices being pre-loaded according to the patient dose and treatment plan with at least one brachytherapy element, wherein each of the plurality of brachytherapy element transfer devices comprises a cannula defining a lumen and a gating feature at least partially occluding the lumen in an occlusive position, the gating feature includes an attachment feature, an arm, and an occlusive feature, and wherein the attachment feature attaches to an outer surface of the cannula by snapping the attachment feature into an indentation on the outer surface of the cannula, and the arm is angled relative to the longitudinal axis of the at least one gating feature so that the occlusive feature is biased into the lumen, and wherein when the gating feature is urged into a non-occlusive position the occlusive feature is urged radially outward from the lumen;

c. inserting a plurality of brachytherapy needles into a region in which the brachytherapy elements are to be implanted in a configuration corresponding to the patient dose and treatment plan;

d. placing a distal end of the cannula of a brachytherapy element transfer device of the plurality of brachytherapy element transfer devices against a proximal end of a corresponding brachytherapy needle of the plurality of brachytherapy needles such that the brachytherapy element transfer device and the brachytherapy needle are in communication, the brachytherapy element transfer device and the corresponding brachytherapy needle corresponding according to the patient dose and treatment plan; and e. using a stylet, urging the at least one brachytherapy element of the brachytherapy element transfer device against the gating feature of the brachytherapy element transfer device, such that the gating feature is urged into a non-occlusive position while the distal end of the cannula is in contact with the proximal end of the corresponding brachytherapy needle, and then urging the brachytherapy element past the gating feature and from the loaded brachytherapy element transfer device into the corresponding brachytherapy needle;

f. repeating steps d-e for at least one additional brachytherapy element transfer device of the plurality of brachytherapy element transfer devices.

10. The method according to claim 9, further comprising holding the stylet in position while withdrawing the brachytherapy needle from the patient, thereby depositing the at least one brachytherapy element in the patient.

11. The method according to claim 10, wherein the stylet is at least as long as the combined length of the brachytherapy element transfer device and the corresponding brachytherapy needle, and holding the stylet in position while withdrawing the brachytherapy needle from the patient, thereby depositing the at least one brachytherapy element in the patient, is done while the brachytherapy element transfer device and the corresponding brachytherapy needle are in contact.

12. The method according to claim 9, wherein the distal end of the cannula is configured to mate securely to the proximal end of the corresponding brachytherapy needle, and wherein placing the distal end of the cannula of the brachytherapy element transfer device against the proximal end of the corresponding brachytherapy needle includes securely mating the distal end of the cannula to the proximal end of the corresponding brachytherapy needle.

13. The method according to claim 9, wherein the gating feature is positioned proximate to the distal end of the cannula, and wherein each of the plurality of brachytherapy element transfer devices further comprises a second gating feature positioned proximate to a proximal end of the cannula, and wherein the at least one brachytherapy element is locked between the first gating feature and the second gating feature until the gating feature is urged into a non-occlusive position, and the brachytherapy element is urged past the gating feature and from the loaded brachytherapy element transfer device into the corresponding brachytherapy needle.

14. A brachytherapy element transfer device comprising:
a hollow cannula defining a lumen, wherein a distal end of the cannula is configured to be secured to a proximal end of a brachytherapy device such that the distal end communicates with the proximal end of the brachytherapy device; and
a first gating feature including a first attachment feature, a first arm, and a first occlusive feature, wherein the first attachment feature is attachable to an outer surface of the cannula by snapping the attachment feature into place at least partially around the outer surface of the cannula, and wherein the arm is angled relative to the longitudinal axis of the at least one gating feature so that the occlusive feature is biased into the lumen to at least partially occlude the lumen in an occlusive position, the occlusive feature capable of being urged radially outwardly to allow a brachytherapy element to pass the at least one gating feature.

15. The device according to claim 14, further comprising a second gating feature, wherein the first gating feature is positioned proximate to the distal end of the cannula and the second gating feature positioned proximate to a proximal end of the cannula, the brachytherapy transfer device configured for loading from a proximal end by inserting one or more than one brachytherapy elements into an opening at the proximal end, urging the one or more than one brachytherapy elements into the second gating feature such that the second gating feature is forced radially outward by the one or more than one brachytherapy elements, and urging the one or more than one brachytherapy elements past the second gating feature until the one or more than one brachytherapy elements are locked between the first gating feature and the second gating feature.

16. The device according to claim 14, wherein the first gating feature is removably attachable from outside the cannula.

17. The device according to claim 16, wherein the second gating feature is removably attachable from outside the cannula separate from the first gating feature.

18. The device according to claim 14, further comprising a grip that is seamlessly brazed to an outer surface of the cannula.

* * * * *